(12) United States Patent
Buckman et al.

(10) Patent No.: US 8,480,693 B2
(45) Date of Patent: *Jul. 9, 2013

(54) METHOD AND DEVICE FOR TEMPORARY EMERGENCY VESSEL ANASTOMOSES

(75) Inventors: Robert F. Buckman, Radnor, PA (US); Jay A. Lenker, Laguna Beach, CA (US); Donald J. Kolehmainen, Laguna Niguel, CA (US)

(73) Assignee: Damage Control Surgical Technologies, Inc., Laguna Beach, CA (US)

( * ) Notice: Subject to any disclaimer, the term of this patent is extended or adjusted under 35 U.S.C. 154(b) by 1542 days.

This patent is subject to a terminal disclaimer.

(21) Appl. No.: 12/070,697

(22) Filed: Feb. 19, 2008

(65) Prior Publication Data

US 2008/0294084 A1    Nov. 27, 2008

Related U.S. Application Data

(63) Continuation of application No. 10/703,220, filed on Nov. 5, 2003, now Pat. No. 7,335,215.

(60) Provisional application No. 60/424,038, filed on Nov. 5, 2002.

(51) Int. Cl.
*A61B 17/08* (2006.01)

(52) U.S. Cl.
USPC .......................................... 606/153

(58) Field of Classification Search
USPC ........................................ 606/153, 154, 213
See application file for complete search history.

(56) References Cited

U.S. PATENT DOCUMENTS

| | | | |
|---|---|---|---|
| 3,683,296 A | 8/1972 | Sueulei | |
| 4,657,019 A | 4/1987 | Walsh et al. | |
| 5,141,516 A | 8/1992 | Detweiler | |
| 5,588,949 A | 12/1996 | Taylor et al. | |
| 5,925,054 A * | 7/1999 | Taylor et al. | 606/153 |
| 5,947,919 A * | 9/1999 | Krueger et al. | 604/8 |
| 6,071,297 A * | 6/2000 | Salahieh et al. | 606/198 |
| 6,152,937 A | 11/2000 | Peterson et al. | |
| 6,214,022 B1 * | 4/2001 | Taylor et al. | 606/153 |

* cited by examiner

*Primary Examiner* — Katherine Dowe
*Assistant Examiner* — Michael Mendoza (57) ABSTRACT

A device and method for achieving hemostasis and leakage control in vascular structures and other body ducts or vessels in an emergency room or trauma situation. The device has at least one shunt that contains an obturator on an end of the shunt. The shunt is inserted into a damaged vessel or lumen for sealing the leak or hemorrhage. Two shunts that both contain obturators on one of their ends can be inserted into two different vessels or lumens when the vessel or lumen has been severed. The obturators allow for the improved ease of insertion into the vessel or lumen. The two shunts are then releasably attached to restore fluid communication through the vessel or lumen. The shunt is placed temporarily within the patient and then removed when definitive repair can be achieved by a qualified physician.

20 Claims, 10 Drawing Sheets

Fig. 10C ness of the inventions described below will become apparent to those skilled in the art upon review of the specification and the accompanying drawings.

METHOD AND DEVICE FOR TEMPORARY EMERGENCY VESSEL ANASTOMOSES

PRIORITY CLAIM

This application is a continuation of U.S. patent application Ser. No. 10/703,220, filed on Nov. 5, 2003 now U.S. Pat. No. 7,335,215, which claims priority benefit under 35 USC §119(e) from U.S. Provisional Application No. 60/424,038 filed Nov. 5, 2002.

FIELD OF THE INVENTIONS

The inventions described below relate the field of treating vascular hemorrhage via anastomoses of severed or damaged vessels in an emergency room or trauma situation.

BACKGROUND OF THE INVENTIONS

As recently as the early 1990s, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguination, or postoperatively, due to the complications of prolonged shock and massive transfusion to replace blood lost as a result of the trauma.

One of the most notable developments in the recent evolution of surgery has been the introduction of the concept of staged laparotomy to overcome the deficiencies of the repair all-at-once approach. This new strategy of staged laparotomy employing new tactics that have been termed "Damage Control" is now used in 10% to 20% of all trauma laparotomies. During damage control procedures, time is of the essence. Every minute that passes without hemostatic control, leads to further blood loss, shock and risk of intra-operative exsanguination. In damage control operations it is important to contain or stop, as quickly as possible, hemorrhage from major wounds to the blood vessels. Additionally, it is important to quickly stop spillage from body ducts and lumens such as the bile duct.

Devices and methods of control for hemorrhage from solid organs, viscera, body ducts, and vasculature are desirable in order to minimize damage to the patient as a result of the trauma. Typical vascular injuries requiring hemostatic control may include, for example, a wound to the descending abdominal aorta, the iliac arteries and veins, superior mesenteric vessels, vena cava or the portal vein, renal arteries and veins, superficial femoral artery, popliteal artery, ulnar arteries and lumbar arteries. The existing methods for controlling these include clamping and sewing, or compressing the vessel until ischemia occurs. All these current methods have the potential for tissue necrosis as they do not permit blood flow to continue through the wounded vessel once hemorrhage has been stopped.

Although there are procedures for controlling these injuries, their use has been hampered due to the lack of utilization of optimal devices or tactics in their execution. Each area offers technological opportunities to improve the devices and procedures for applying those devices. While existing methods and procedures, including the use of standard vascular instruments, vascular clamps, sutures, and tourniquets do allow the rapid control of vascular and visceral injuries in many cases, the standard techniques and tools have not been designed for temporary placement as part of a staged operation. Specifically, tourniquets, forceps, vessel clamps or clips can lead to tissue necrosis due to ischemia, and sutures 'take a long time to apply and are generally not appropriate in a damage control or emergency setting. Vascular shunts such as the Javid shunt and the Argyle shunt exist but are not suitable for emergency application on the hemorrhaging patient. They are primarily intended for use in carotid procedures. New devices, procedures and methods are needed to support the strategy of damage control in patients who have experienced vascular injury. Such devices and procedures are particularly important in the emergency, military, and trauma care setting. These limitations have been overcome by the new device and method described below.

SUMMARY OF THE INVENTION

This device and methods described below relate to repair of damaged blood vessels and body ducts. An anastomosis device or shunt is capable of sealing a leak or hemorrhage in an artery, vein or body duct while still maintaining an open central lumen. The open central lumen is necessary to permit the contents of the blood vessel or duct to reach its destination, thus the physiology is maintained.

When a blood vessel becomes wounded or severed, the loss of blood must be stopped or severe blood loss will occur. Severe blood loss could lead to exsanguination and death of the patient. It could also lead to shock and a cascade of deteriorating physiological conditions with negative short and long-term effects on the patient. In addition, the tissues downstream of the damage may become ischemic, a condition that could potentially lead to tissue necrosis or compromised organ function.

Emergency repair of severed blood vessels preferably includes immediate repair of the damage and restoration of patency to the blood vessel. Such immediate repair is not generally available in the emergency or military setting as it requires a skilled vascular or general surgeon and the facilities of a hospital surgical suite to repair the vessel or duct. Surgeons and well-equipped surgical suites are not available except following transport to such facilities by ambulances, helicopters, mobile intensive care units (MICU) and the like.

Thus, a Damage Control approach is appropriate for this type of repair. A temporary repair can be made by a somewhat less trained caregiver, and in less equipped setting, if adequate tools are available. Such temporary repair entails the placement of a shunt across the wound to stop the hemorrhage and serve as a conduit through which the contents of the vessel or duct may travel to distal locations where this fluid is needed. The shunt is temporarily placed. Preferably, within a week of implantation, the temporary emergency shunt is removed and definitive repair is accomplished by a vascular surgeon or endovascular repair specialist.

The shunt includes at least one elongate tubular structure that is inserted into the ends of the damaged vessels or ducts. This single tube shunt is preferable for repair of damaged but not severed vessels or ducts. At the insertion end of the shunt is an obturator. Difficulty in quickly inserting the shunt in to the blood vessel is overcome by application of the obturator. The obturator is a tapered, pointed or rounded central structure that serves to center the shunt inside the vessel and allows the shunt to be shoehorned into the vessel. Once the shunt is in the correct place, the obturator may be removed from the shunt. The obturator may be a cage-like device that is of low cross-sectional profile and is left in place so it need not be removed. Alternatively it could be configured with a taper at the end inserted into the blood vessel that can expand to minimize projections into the vessel lumen. This configuration allows the shunt to be inserted without the additional steps of removing the obturator. If it is not desired to use an obturator, the distal end of the shunt may be configured of an angled exterior edge. This angled exterior edge serves to permit the shunt ends to be inserted into the damaged or severed ends of the vessel or lumen without the need for an obturator. In addition, the angled ends minimize the risk that tissue ingrowth will be sufficient to stenose the shunt at its ends. The shunt may be used in conjunction with, or include guide wires that are slidably disposed through a lumen of the shunt or are integrally disposed at the tip of an obturator or nose cone.

The single tube shunt is advantageously utilized as a single tube between the ends of the damaged vessel or duct. The single tube approach minimizes projections and detents on the interior lumen of the shunt that could serve as a nytus for thrombus or emboli generation. This single shunt can be made of any flexible polymeric structure with kink resistance and crush resistance. Kink and crush resistance are created by embedding woven, spiral, or braided structures into the wall of the graft. These reinforcing structures are not exposed on the interior of the shunt. The tube can be long enough to form a loop so that length adjustability is not a problem. The ends of the loop shunt are inserted into the damaged region of vessel with enough diameter to seal against the wall of the undamaged part of the vessel or duct. The remainder of the shunt forms a loop that serves as a sizing means or an expansion loop to accommodate patient movement.

One or more clamps may then be applied to hold the vessel or duct against the shunt inserted therein. The clamps serve to keep the vessel or duct attached to the outside of the shunt. The outer surface of the shunt may have detents, rings, circumferential depressions or ridges that facilitate frictional stability between the vessel or duct lumen and the exterior wall of the shunt. Several different types of clamps may be utilized in this configuration. Simple spring-loaded semi-circular/or circular components that are openable and then close under elastomeric or spring tension are appropriate. Alternatively, the clamps may be fabricated so that they pass around the vessel and are mechanically compressed by a locking mechanism. Another type of clamp may be comprised of elastomeric tubes that are rolled back toward the center mating area of each half of the shunt. The elastomeric tubes are unrolled over the ends of the severed vessel to maintain clamping force on the vessel. The force of the clamp is such that ischemia and necrosis of the vessel or duct wall does not occur.

The side of the shunt may include a side port communicating between the outer surface or the shunt and the interior lumen. This side port is suitable for injection or withdrawal of heparin, saline, air or other medications or fluids, into the shunt.

Additionally, the shape of the distal end of the shunt, or the edge that interfaces with the body vessel or lumen, may be configured differently. The shunt distal ends may be configured to minimize or eliminate any ledges or ridges at the vessel or body lumen interface. The distal edges can be flared outward from the inside to form a sharp edge at the vessel interface and at a diameter equal to or slightly larger than that of the undistended vessel internal lumen. In this way, no edges present themselves for the buildup of thrombus and the sharp edge does not cause significant tearing forces on the vessel or lumen wall such as might cause further damage or tissue hyperplasia.

The shunt is, preferably, pre-sterilized. The shunt is, preferably, packaged in a double aseptic package to facilitate sterile usage. The tube is fabricated from polymeric materials such as, but not limited to, polyester, PTFE, polyimide, and the like. The tube, especially the internal lumen, is preferably coated with anti-thrombogenic materials such as heparin to minimize the risk of thrombosis or embolization. The shunts are, at least partially, radiopaque or comprise radiopaque components and can be visualized on fluoroscopy or X-ray. This feature is important in locating shunts on subsequent follow-up.

A dual tube shunt may also be utilized where the vessel or lumen has been severed and not merely damaged. This configuration consists of two identical tubes, each for insertion into one of the severed portions of the vessel or lumen. Each of the tubes may have their own obturators. Each tube is inserted into an end of the damaged blood vessel. The obturators are, if appropriate, removed from the tube members and the shunts and the shunt components are sealably attached to each other. Quick release type connections such as bayonet mounts or snap clips facilitate bringing the two ends of the shunt together. Gaskets or fluid-tight seals at the interface between the quick-release connections prevent blood or fluid loss once the shunts are connected together.

A method of insertion of the shunt within the vasculature is also disclosed. In the case where the vessel is fully severed, a surgical incision is made to access the two vessel ends. The two vessel ends are brought to within proximity of each other. A large clamp or clamps are applied to maintain the two vessel ends within close proximity during the procedure and to maintain hemostasis. The obturator of a shunt end is inserted into one of the vessel ends and the obturator of the other shunt end is inserted into the second vessel end. Clamps are applied around the blood vessel ends to maintain the shunt ends within the vessel. The two obturators are removed, the two shunt ends are sealingly engaged together and locked together. The area around the shunt is de-aired and the clamp or clamps removed. Injection of heparin into the area of the shunt helps minimize the risk of thrombosis or emboli during or immediately after the procedure. De-airing is preferably accomplished through a side port that comprises a seal, which may be penetrated by a hollow needle of a syringe, but closes once a de-airing syringe and needle are removed from the port.

This method is slightly different where the vessel is damaged but not completely severed. A clamp is placed around the vessel to completely seal the vessel in the region of the damage. The clamp also serves to prevent further damage to the vessel by tearing or tension. One end of a long shunt is inserted into the damaged region or an incision made somewhere near the damage. The shunt end is clamped onto the vessel end. The other end of the long shunt is inserted near the damaged region or in the damaged region so as to carry blood from the proximal end of the wound to the distal end of the wound. The long shunt may include a loop that permits length adjustment and facilitate insertion of the shunt ends into the damaged vessel. Suitable vessel clamps are applied to the vessels around the shunts to keep the shunt ends in place and sealed to the vessels. The vessel is de-aired and the large vessel clamps are removed. Heparin or other medication is injected, as required.

DETAILED DESCRIPTION OF THE INVENTIONS

Figure 1A:
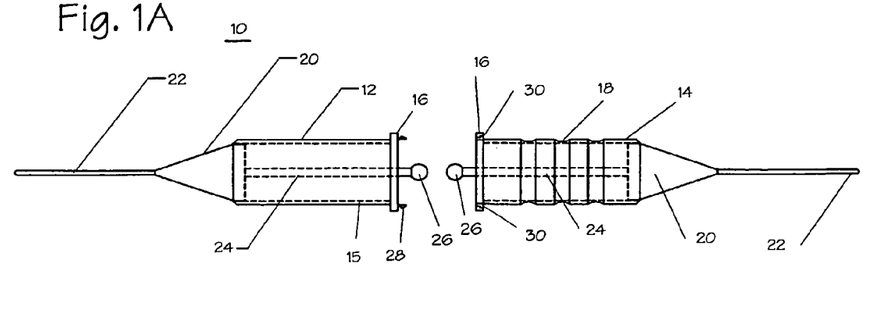
FIG. 1A illustrates a side view of two components of the shunt in its separated state with the obturators in place.

FIG. 1A illustrates a shunt 10 of the present invention comprising an axially elongate left tube 12, an axially elongate right tube 14, a plurality of flanges 16, a plurality of optional friction detents 18, a plurality of obturators 20, a plurality of optional guidewires 22, a plurality of obturator rods 24, a plurality of obturator handles 26, a plurality of locking pins 28, and a plurality of locking recesses 30. The left tube and the right tube further comprise an inner surface 15.

Referring to FIG. 1A, the left tube 12 and right tube 14 are affixed to the flanges 16. The interior surface 15 of the right tube and the left tube is integral to the left and right tubes, respectively, or it may be adhered to these tubes. The friction detents 18 are depressions or ridges circumferentially disposed on the exterior of the left tube and the right tube. The obturators 20 have a tapered end and a blunt end with the tapered end pointing out of the tubes and at the ends away from the flanges. The obturators are slideably engaged within the interior of the left tube and the right tube and are capable of being removed by withdrawing them out at the flange end of the tubes. The guidewires 22 are permanently affixed to the tips of the obturators. The obturator rods 24 are permanently affixed to the blunt end of the obturators and the obturator handles 26 are permanently affixed to the end of the obturator rods away from the obturator. The locking pins 28 are projections from the flange and are permanently affixed thereto. The locking recesses 30 are holes in at least one of the flanges that mate with the locking pins. The shunt is a two-piece device with a right tube and a left tube. The left tube and the right tube are brought together and locked at the flanges by way of locking pins and locking recesses. The obturators, the guidewires, the obturator rods and the obturator handles are removable and intended to be in place only during storage and insertion of the shunt into a blood vessel or other body lumen. The obturators provide a smooth tapered distal surface to each shunt tube and so that these tubes can be manually or robotically inserted into a blood vessel or other body lumen easily. The obturators, in effect, provide a shoehorn effect to allow the shunt to be placed. This is especially important since the exterior surface of the left tube and the right tube are intended to form a press fit into the blood vessel or other body lumen. The left tube and the right tube need to engage the blood vessel in a sealing fashion so the outer diameter of the tubes and may be slightly smaller than, the same size as, or slightly larger than the internal diameter of the body vessel or lumen.

The left tube and the right tube are fabricated from materials such as, but not limited to, ePTFE, PTFE, polypropylene, polyethylene, PEBAX, PET, polylactic acid, polyglycolic acid, silicone, polysulfone, polyimide, and the like. The material is extruded, molded, machined, woven as fabric, knitted as fabric, expanded and sintered, or fabricated using any manufacturing process for such structures. The interior surface is maintained extremely smooth but, in larger diameters, some roughness such as is found in woven materials is acceptable. The interior surface is optionally coated with heparin or other anti-thrombogenic agent. The exterior surface of the shunt is, optionally, coated with an antimicrobial agent such as, but not limited to, iodine, silver azide, or other material or chemical.

The locking pins 28 project from the flanges 16 and fit into the locking recesses 30 on the opposite flange. Tapered front ends on the locking pins allow the locking pins to slide into the locking recesses. The locking pins further comprise a stem that is able to flex somewhat to allow for resilient off-axis movement of the front end of the locking pins. A ledge on the back end of a feature near the front end of the locking pins catches on a mating surface within the locking recesses to hold the two flanges together. Alternatively, the flanges do not project radially beyond the exterior surface of the left tube or the right tube. The flanges, locking pins and locking recesses are fabricated from the same materials as those used for the left tube or the right tube. Other locking mechanisms are appropriate for this application. For example, simple spring clips may be placed over the flanges to hold them together. A bayonet mount, threaded attachment or any other suitable attaching mechanism is appropriate for connecting the right tube to the left tube.

The friction detents 18 provide resistance to separation between the shunt and the internal diameter of the body vessel or lumen into which the shunt is inserted.

Figure 1B:
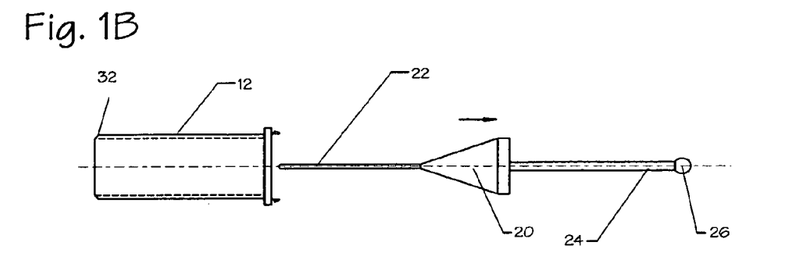
FIG. 1B illustrates a side view of one component of the shunt with the obturator being removed.

FIG. 1B illustrates the left tube 12 further comprising an inwardly tapered distal end 32. The obturator 20, along with the integral guidewire 22, the obturator rod 24 and the obturator handle 26 are shown being withdrawn proximally out of the left tube. The obturator and the other components are removed after the left tube is firmly placed within the inner lumen of a damaged, or preferably severed, blood vessel. Removal of this obturator allows for blood or other fluid flow within the left tube without restriction.

Figure 1C:
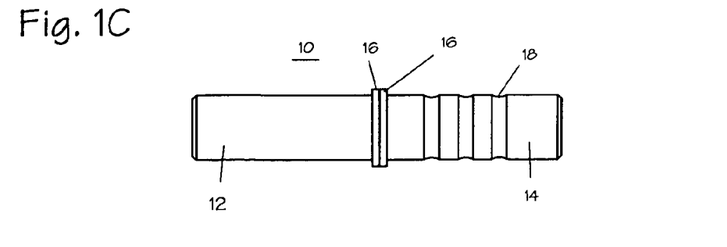
FIG. 1C illustrates a side view of the shunt with its two components in the connected state with both of the obturators removed.

FIG. 1C illustrates a side view of the shunt 10 with the left tube 12 and the right tube 14 connected at flanges 16. The friction detents 18 are shown on the right tube. The locking pins 28 are engaged within the locking recesses 30. The interior surface 15 of the left tube and the interior surface of the right tube mate with little or no macroscopic groove, misalignment, bump, diameter change or roughness. Such accurate and defect-free alignment of the tube interior ensures that this anastomosis point will not be a site for thrombus or generation of emboli.

Figure 2A:
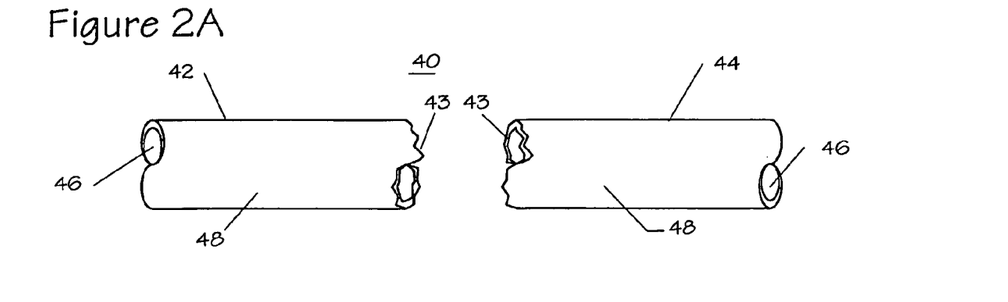
FIG. 2A illustrates a side view of a severed vessel.

FIG. 2A illustrates a severed blood vessel or body lumen 40. The severed vessel further comprises a left side 24, a right side 44, an interior surface 46, an exterior surface 48 and a damage region 43.

Figure 2B:
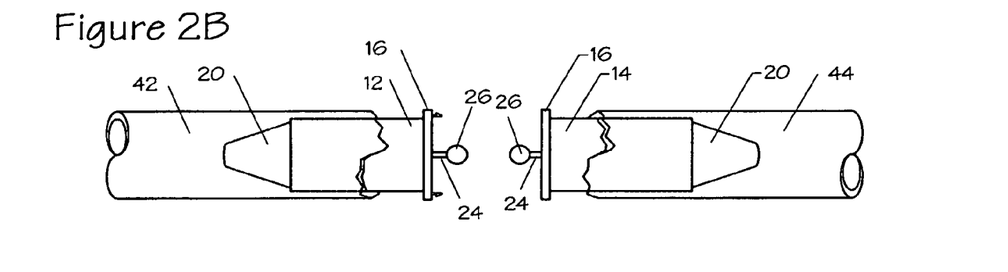
FIG. 2B illustrates a side view of a severed vessel with a shunt component and obturator inserted into each of the ends of said vessel.

FIG. 2B illustrates a side view of the severed blood vessel or body lumen 40 of FIG. 2A with the left tube 12, the flange 16, the obturator 20, the obturator rod 24, and the obturator knob or handle 26 inserted into the left side 42 and the right tube 14, the flange 16, the obturator 20, the obturator rod 24, and the obturator knob or handle 26 inserted into the right side 44.

Figure 2C:
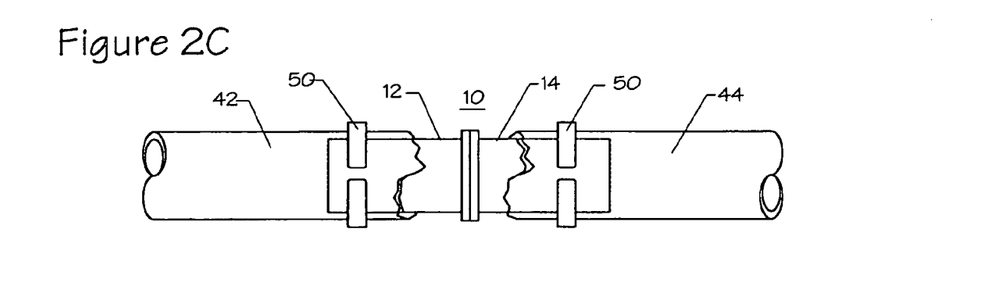
FIG. 2C illustrates a side view of the severed vessel with the obturators removed, the shunt components brought into sealing contact and exterior clamps applied to the vessel.

FIG. 2C illustrates a side view of the left side and the right side of the severed blood vessel or body lumen of FIG. 2A and the shunt connected. The shunt connection to the left side and the right side is further secured with clamps 50. The left shunt tube is inserted into the left body vessel or lumen at the severed region. The right shunt tube is inserted into the right body vessel or lumen at the severed region. The left and right shunt tubes, and, respectively, are inserted far enough that a good friction fit is obtained with the interior surface of the blood vessel. Clamps are applied around the severed ends of the blood vessel so that the left vessel and the right vessel are firmly and frictionally engaged to the exterior surfaces of the shunt ends. The shunt tubes are sealingly engaged in FIG. 2C so that there is no leakage at the interface between the two shunt tubes. In addition, there is no leakage of blood between the left shunt tube and the left vessel end, nor is there leakage of blood between the right shunt tube and the right vessel end. The clamps pass around the vessel ends and provide radially inward pressure on the left vessel end and right vessel end so that these vessel ends are squeezed against the outer surface of the shunt tubes. The clamps are of the spring C-ring type that is separated slightly and then placed over the tubular structure. The elastomeric nature of the clamps is such that the clamps apply a known or controlled force to the tissue of left vessel and right vessel. The clamps have a wide footprint to distribute pressure so as not to damage the tissue of the blood vessel or body lumen or cause necrosis of this tissue. The clamps compress the body vessel or lumen into the shunt. The clamps may also be of a hinged type with a spring bias to force them closed and mechanical advantage to open the clamps. In order to minimize projections from the clamp, it is preferable to place the clamp around the vessel by first opening the clamp with an instrument such as Kocher or Allis clamp that provides mechanical advantage. Minimizing projections improves the implantability of the clamp.

The clamps 50 are preferably fabricated from stainless steel, titanium, nitinol, Elgiloy or other metal. The clamps may also be fabricated from materials such as, but not limited to, polypropylene, polyurethane, polyethylene, PET, polysulfone, polyimide, and the like. The interior surfaces, or vessel contact regions of the clamp are preferably fabricated from a soft material with low durometer such as silicone elastomer, polyurethane, foam or other material that can distribute forces. These interior vessel contact regions are the vessel contact components of the clamp jaws.

Figure 3A:
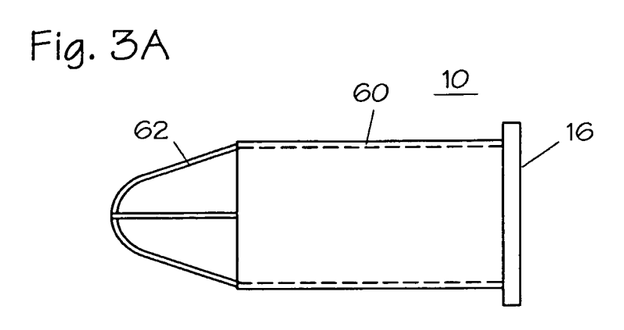
FIG. 3A illustrates another embodiment of a shunt component and a strut-type obturator, wherein the obturator is not removable from the shunt component.

FIG. 3A illustrates another configuration of the shunt 10. Here, the left tube 60 of the shunt is shown. The left tube of the shunt further comprises an obturator 62 and a flange 16. The obturator is a cage-like structure, fabricated from metal or polymeric materials. Suitable metals include, but are not limited to, cobalt nickel alloys, stainless steel, titanium, tantalum, nitinol, Elgiloy, platinum, gold, platinum-iridium alloys, and the like. Suitable polymers include, but are not limited to, PET, PETG, polyethylene, polypropylene, polyimide and the like. The cage-like obturator is affixed to the distal end of the left tube and is non-removable. The cross-sectional configurations of the bars or struts of the obturator are, for example, circular, elliptical, or configured like an airfoil with a tapered trailing edge. The cross-sectional configuration of the obturator bars or struts is such that narrowing occurs in the direction perpendicular or lateral to the axis of the left tube. The materials of the obturator are highly polished and very smooth to avoid thrombo-emboli generation or thrombus formation. The obturator is generally configured to form a tapered or rounded distal end to facilitate wedging the distal end of the left tube into a damaged blood vessel that has been severed or incised to permit such insertion. The right side of the shunt, not shown, is configured similarly with a nonremovable obturator or other type of obturator.

Figure 3B:
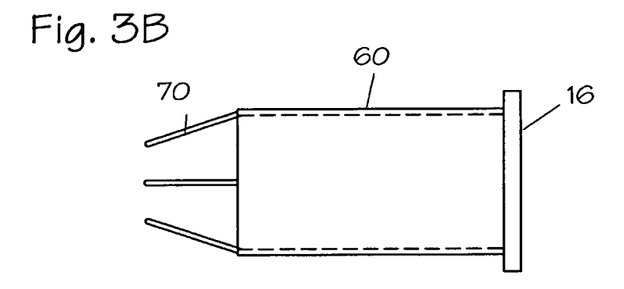
FIG. 3B illustrates yet another embodiment of a shunt component with a tapered strut-type obturator that does not require removal following placement.

FIG. 3B illustrates another configuration of the left shunt tube 60 where the obturator 70 is non-removable. The left shunt tube is shown, further comprising a non-removable obturator and a flange 16. The material used for the nonremovable obturator is, preferably, shape memory metal such as, but not limited to, nitinol. The nitinol is pre-formed so that in its martensitic phase, the obturator struts are formed or directed into a cone shape, bullet shape or tapered shape suitable to guide the distal tip of the left shunt tube into the damaged or incised blood vessel. The austenite finish temperature is, preferably between room temperature of 22 degrees Centigrade and body temperature of 37 degrees Centigrade. Preferably, the austenite finish temperature is between 26 degrees Centigrade and 34 degrees Centigrade.

The individual struts of the obturator are not connected at the distal tip, or apex, so as to permit later outward motion of the struts. The obturator comprises a plurality of struts, sufficient to shoehorn or guide the left shunt tube into the blood vessel. The struts are permanently affixed to the left tube and that fixation supports the struts so that when they change shape, the shape change is relative to the fixed orientation of the shunt tube. When the obturator is exposed to warm blood at 37 degrees centigrade, the shape memory material moves to an austenitic state and the struts flex outward to form a tube parallel with the walls of the left shunt tube. Referring to FIGS. 2A, 2B, 2C and 3C, the struts no longer project into the lumen of the body vessel or lumen 40. In yet another embodiment, the struts of the obturator 70 open further than parallel with the left shunt tube 60 so as to provide a radial gripping mechanism on the damaged blood vessel into which the shunt end is inserted. This design has the advantage of not needing to be removed once the shunt end is placed within the vessel. The right shunt tube would be similarly configured as the left shunt tube, shown, and would sealingly engage the left shunt tube.

Figure 3C:
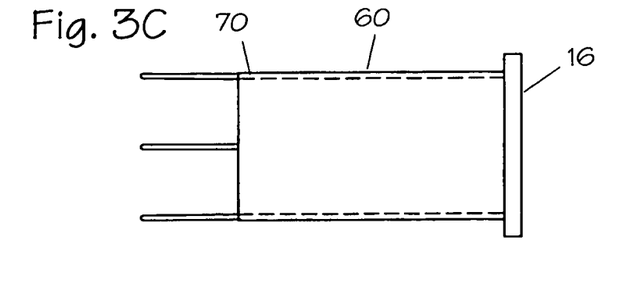
FIG. 3C illustrates the shunt component of FIG. 3B wherein the tapered strut-type obturator has expanded following placement in the vessel.

FIG. 3C illustrates the left shunt tube 60 as disclosed in FIG. 2B where the obturator 70 struts have rotated outward and aligned themselves parallel to the wall of the blood vessel or axis of the shunt tube. The flange 16 is on the side of the shunt tube away from where the shunt tube is inserted into the vessel.

Alternatively, the struts of the obturator can be configured to form an inward taper in their martensitic phase and form a straight or outward taper in their austenitic phase. However, the austenite finish temperature would be raised to or above body temperature 37 degrees Centigrade so that electricity or Ohmic heating would be used to raise the temperature of the obturator to a temperature above this austenite finish temperature. Hysteresis would maintain the opening of the obturator struts.

Additionally, the struts can be individually and slideably mounted within the left shunt tube 60. A connecting cable or linkage is provided to withdraw each strut within the left shunt tube so that the struts do not project beyond the distal tip of the left shunt tube. The right shunt tube would be similarly configured as the left shunt tube shown.

Figure 4A:
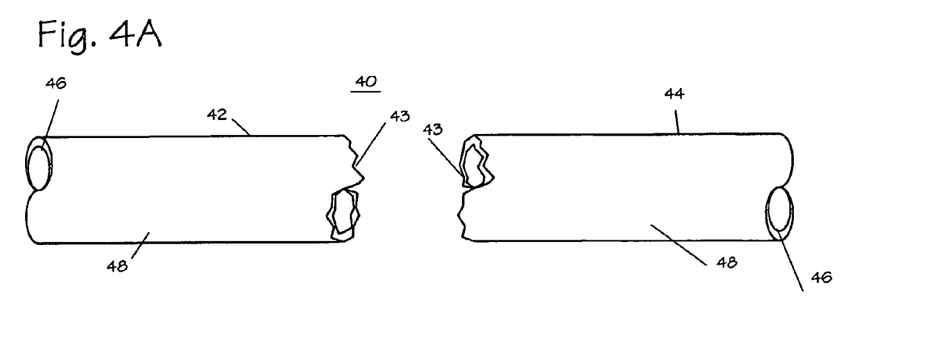
FIG. 4A illustrates a body vessel or lumen that has become severed.

FIG. 4A illustrates a severed blood vessel or body lumen 40. The severed vessel further comprises a left side 42, a right side 44, an interior surface 46, an exterior surface 48 and a damage region 43, which in this case is a complete severing tear through the vessel.

Figure 4B:
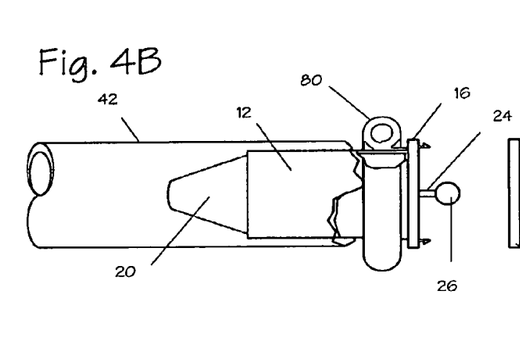
FIG. 4B illustrates a shunt component further comprising an obturator and a roll clamp in its retracted state.

FIG. 4B illustrates the left side of a damaged body vessel or lumen that has left shunt tube 12 inserted therein. The left shunt tube further comprises an obturator 20, a flange 16, an obturator rod 24, and an obturator handle 26. The left shunt tube 12, still further comprises a roll clamp 80. The roll clamp is shown in its retracted or rolled position. The roll clamp is a tubular structure fabricated from elastomeric materials that are attached to the left shunt tube 12 at or near the flange 16. After the left shunt tube and its obturator 20 are inserted into the severed end of the left damaged blood vessel or body lumen 42, the roll clamp is unrolled to cover and compress the vessel end around the exterior of the left shunt tube. The roll clamp is fabricated from materials such as, but not limited to, polyurethane, silicone elastomer, C-Flex, thermoplastic polymer, latex rubber, synthetic polyisoprene, and the like. The roll clamp material is typically from 0.005 inches to 0.1 inches thick and preferably from 0.010 to 0.050 thick. The unstretched inner diameter of the roll clamp is such that it at least as small in diameter as the outer diameter of the left shunt tube. This diameter ensures good elastic compression around the blood vessel or lumen to maintain it secured to the left shunt tube. Smaller inner diameters of the unstretched roll clamp may be appropriate depending on the elastic force of the material used in fabrication of the clamp.

Figure 4C:
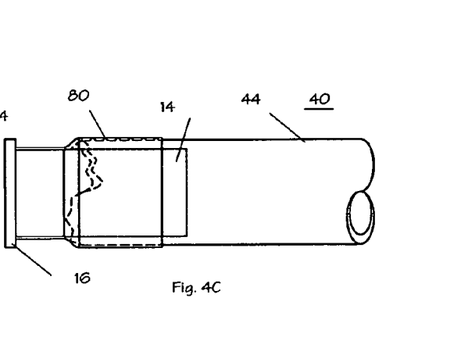
FIG. 4C illustrates a shunt component with the obturator removed and further comprising the roll clamp in its deployed state.

FIG. 4C illustrates the right side 44 of the severed blood vessel or body lumen 40. The right shunt tube 14 is inserted therein. The flange 16 is not inserted within the blood vessel 44. The obturator, the obturator shaft, and obturator handle have been removed from the right shunt tube 14 and are not shown in FIG. 4C. The roll clamp 80 has been deployed or unrolled over the end of the vessel to compress the vessel around the right shunt tube.

Figure 4D:
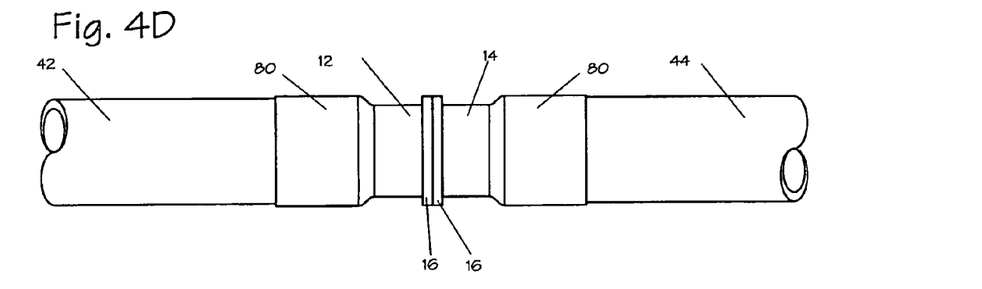
FIG. 4D illustrates two shunt components, each one inserted into one end of a severed body vessel or lumen with the roll clamps deployed and the shunt components brought into sealing contact.

FIG. 4D illustrates the right 44 and left 42 sides of the severed blood vessel or body lumen 40 with the left shunt tube 12 and the right shunt tube 14 inserted therein. The left shunt tube and the right shunt tube are further sealingly connected at the flanges 16 and the obturators 20, obturator rods 24 and the obturator handles 26 are removed prior to connecting the flanges 16 together. The left and right roll clamps 80 are shown fully deployed in this figure. The roll clamps of this configuration are integral to the shunt tubes and thus, are not easily lost, dropped or misplaced. The roll clamps are also less traumatic to tissue and will cause less damage than spring-loaded clamps 50 placed around pinch points on the severed sections of body vessel or lumen.

Figure 5A:
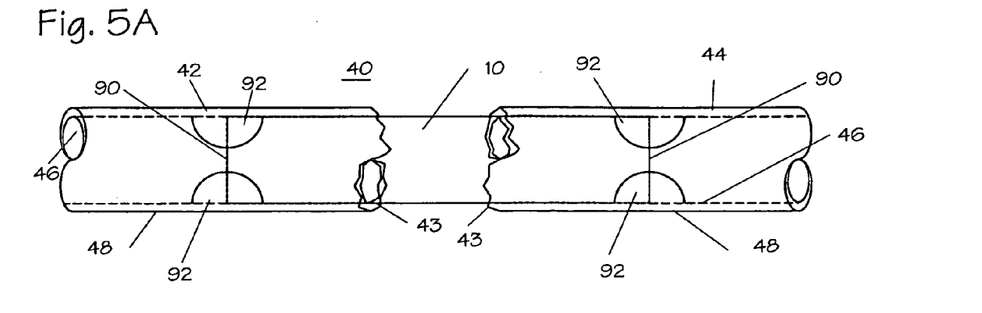
FIG. 5A illustrates a body vessel or lumen that has become cut all the way through with a shunt inserted and the shunt having straight cut ends.

FIG. 5A illustrates a severed blood vessel or body lumen 40 with its ends connected by a tubular shunt 10. The shunt further comprises perpendicular or laterally cut ends 90. The severed body lumen or vessel further comprises a left side 42, a right side 44, an interior surface 46, an exterior surface 48 and a damage region 43. Thrombus buildup 92 causes significant annular narrowing or stenosis of the lumen of the vessel.

Figure 5B:
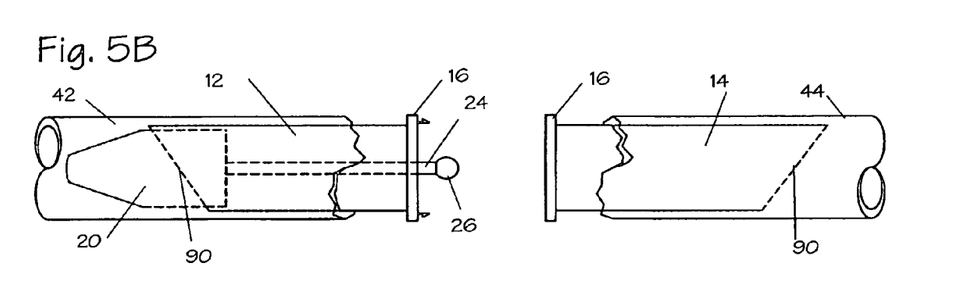
FIG. 5B illustrates the body vessel or lumen of FIG. 5A with shunt components inserted therein.

FIG. 5B illustrates the same severed body vessel or lumen as shown in FIG. 5A, but a shunt tube with angled distal ends 90 and a left side obturator 20, an obturator shaft 24 and an obturator handle 26 is inserted into the left vessel end 42. The right vessel end 44 has a shunt tube 14 inserted into its lumen. The flanges 16 are on the ends of the tubes 12 and 14 away from their respective vessel ends. The right tube has an angled distal end and, thus, is able to be inserted into the vessel end without the need for an obturator.

Figure 5C:
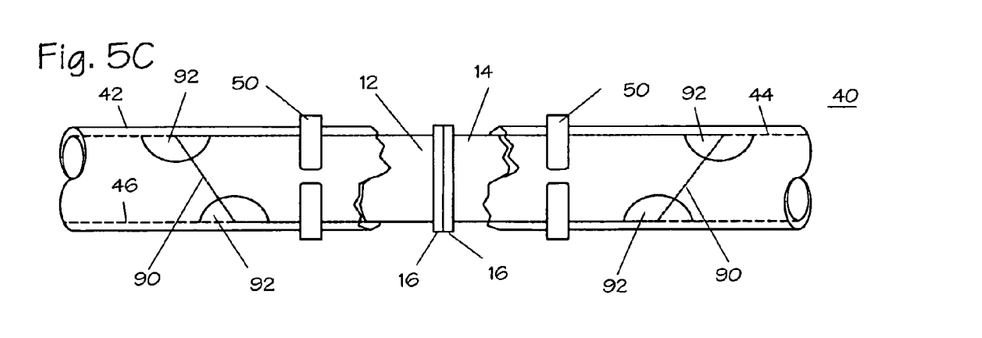
FIG. 5C illustrates the body vessel or lumen of FIG. 5A with the obturator of FIG. 5B removed from the left component and both components brought within sealing contact.

FIG. 5C illustrates the severed vessel with the shunt inserted therein and connected to join the two vessel ends at the flanges. A pair of clamps 50 are applied to the vessel ends 42 and 44 to hold the shunt tubes in place. Thrombus buildup 92 at the distal ends 90 of the shunt is rendered asymmetric within the lumen, thus increasing the through lumen of the vessel 40 and creating less stenosis than if straight perpendicular ends 90 were used on the shunt tubes.

Figure 6A:
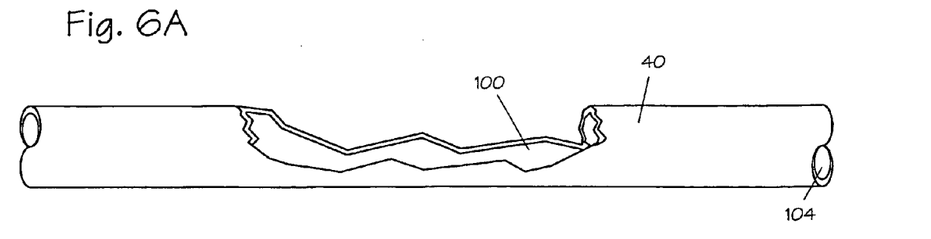
FIG. 6A illustrates a body vessel or lumen that has become damaged but not completely severed.

FIG. 6A illustrates a body vessel or lumen 40 that has become damaged but not severed. A longitudinal tear or rip 100 has occurred in the vessel. In a case such as this, the vessel ends will not have retracted and access to the vessel is much simpler than when the vessel is fully severed.

Figure 6B:
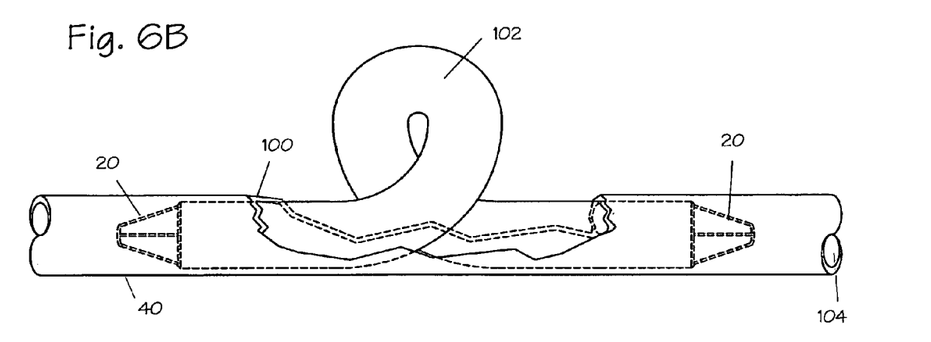
FIG. 6B illustrates the body vessel or lumen of FIG. 6A with a flexible one-piece shunt with non-removable obturators inserted therein.

FIG. 6B illustrates another embodiment of a shunt 102 of the present invention that is of single piece construction. The shunt is inserted into the damaged vessel 40 to stop bleeding and to maintain patency of the lumen 104 of the vessel. The shunt further comprises obturators 20. In this embodiment, the two obturators 20 are of the wire strut type and are non-removable. Any other type of obturator would also be suitable for this embodiment of the graft. A retractable or removable obturator requires linkages or rods running through the shunt and exiting at a point where they can be controlled or manipulated. Shape-memory obturators are also suitable for this embodiment of the shunt. The outer diameter of the shunt is sized to fit tightly into the inner lumen of the vessel so as to make a fluid-tight seal but not so tight as to make the shunt difficult to insert into the vessel.

The shunt is preferably fabricated from flexible materials such as, but not limited to, polyurethane, C-Flex, thermoplastic elastomers, silicone elastomers, expanded polytetrafluoroethylene, polyester, glycol modified polyester, and the like. The shunt is, preferably configured with a smooth interior surface. The wall of the shunt is, preferably, wound with a stainless steel coil or braid to provide for kink resistance and crush resistance. The coil or braid is, preferably totally encased within the wall of the shunt but could be exposed on the external aspect. The internal aspect or surface of the shunt is, preferably always very smooth. The outer wall of the shunt could be configured with corrugations or a spiral structure to impart increased kink-resistance. The shunt further preferably comprises radiopaque markers fabricated from materials such as, but not limited to, stainless steel, tantalum, platinum, iridium, gold or combinations thereof.

Figure 6C:
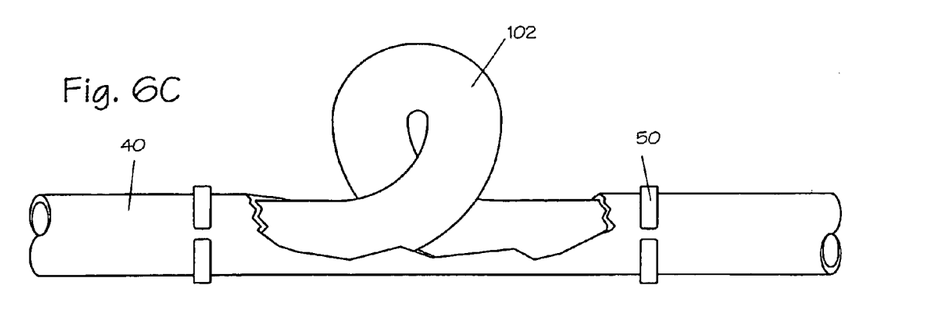
FIG. 6C illustrates the flexible shunt of FIG. 6B inserted into the damaged body vessel or lumen of FIG. 6A and external clamps further applied.

FIG. 6C illustrates the shunt 102 of the present invention inserted into the damaged blood vessel or body lumen 40 at the damage site 100. A plurality of clamps 50 are applied to ensure stability of the junction and seal between the shunt 102 and the vessel 40. The clamps 50 are, preferably, aligned to force the vessel tissue into the friction grooves 18 preferably located on the shunt.

Figure 7A:
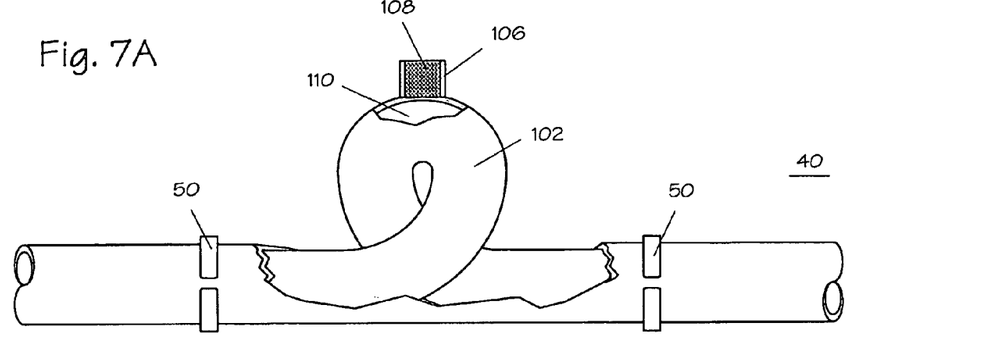
FIG. 7A illustrates a flexible, one-piece shunt inserted into a damaged body lumen or vessel with a side-port.

FIG. 7A illustrates a shunt 102 of the present invention, further comprising a side-port 106 and an interior lumen 110, inserted into a body vessel or lumen 40 which has become damaged but not severed. The side-port further comprises a sealing material core 108. A syringe with a hypodermic needle may be used to inject or remove liquids or air from the interior of the shunt through the side-port. One particularly important use for the side-port is the injection of heparin into the shunt 102 and distal vasculature to prevent emboli occurrence or thrombus buildup. The sealing material core 108 may be easily penetrated by the syringe needle and closes up after removal of the syringe to prevent hemorrhage. The needle penetrates all the way from the exterior of the side-port to the interior lumen 110 of the shunt. Suitable materials for the sealing material core include, but are not limited to, silicone elastomer, polyurethane, foam polymers, C-Flex, and the like. A plurality of clamps 50 are also shown applied around and compressing the wall of the vessel and over the shunt. The side-port provides an excellent access site to inject fluid such as saline to inflate or pressurize the shunt and the body vessel or lumen during insertion of the shunt.

Figure 7B:
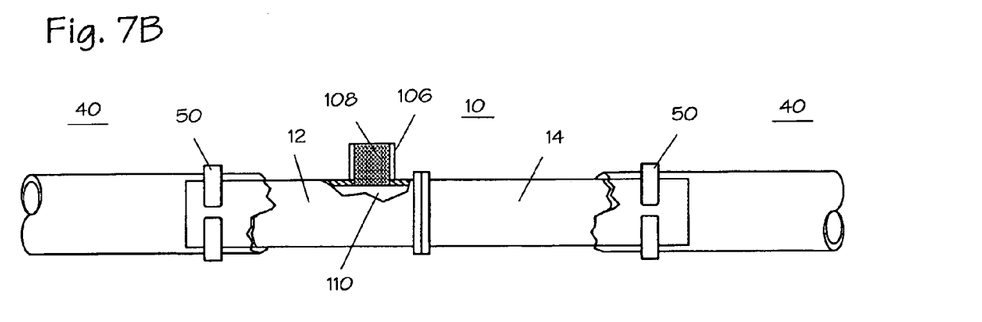
FIG. 7B illustrates a rigid, two piece shunt inserted into a completely separated body lumen or vessel with a side port.

FIG. 7B illustrates a shunt 10, further comprising a left tube 12, a right tube 14, a plurality of flanges 16, a side-port 106, and a central lumen 110. The shunt 10 is two pieces connected at the flanges and inserted into a fully severed blood vessel 40. A plurality of clips 50 are shown applied around the vessel to clamp the vessel securely to the shunt. The side-port operates in the same way as that described above. The side-port is placed on one or both of the shunt ends. Here, the side-port is shown affixed to the left shunt end but it could also be affixed to the right shunt end. Preferably, the side-port is located on the upstream shunt component. The side-port provides a preferred access site to inject fluid such as saline to inflate or pressurize the shunt and the body vessel or lumen during insertion of the shunt.

Figure 8A:
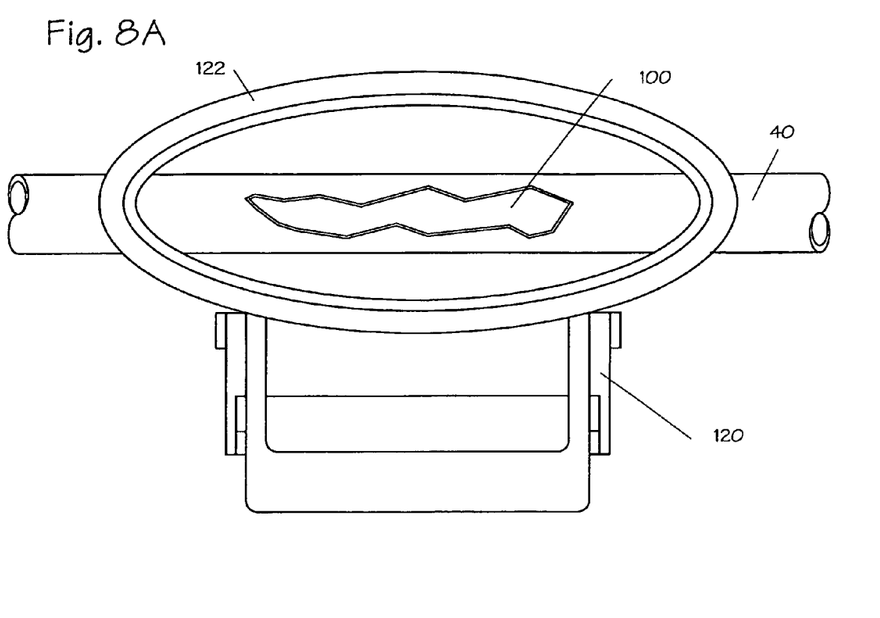
FIG. 8A illustrates a top view of a damaged body vessel or lumen clamped with a large-footprint clamp.

FIG. 8A illustrates a top view of a blood vessel 40 further comprising a damaged area 100 that does not sever the blood vessel 40. A clamp 120 is applied to close off the blood vessel, isolate the wound 100, prevent further hemorrhage, and ensure that the vessel does not completely tear through and separate. The clamp comprises a set of circular or elliptical jaws 122 with a central opening that allows access to the wound or damage site. The central opening of the jaws is preferably large and permits manipulation inside this central opening. The type of clamp preferred for this type of procedure is disclosed in U.S. provisional patent application No. 60/410,635, entitled "Method and Apparatus for Vascular and Visceral Clipping", U.S. provisional patent application No. 60/447,110, entitled "Method and Apparatus for Vascular and Visceral Clipping", and PCT application number US03/28435, entitled "Method and Apparatus for Visceral Clipping," the entire specifications of which are included herein by reference.

Figure 8B:
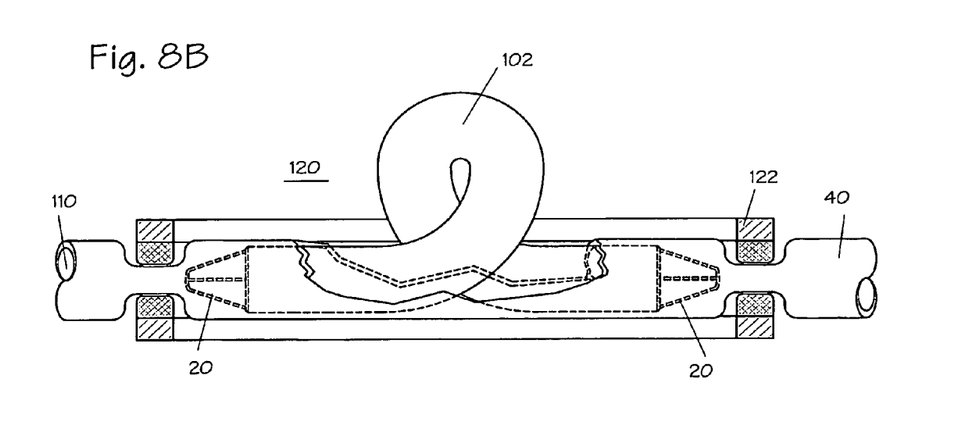
FIG. 8B illustrates a side view of the damaged body vessel or lumen of FIG. 8A with a shunt inserted therein.

FIG. 8B illustrates the blood vessel 40 of FIG. 8A in a side view with the jaws 122 of clamp 120 pinching off the internal lumen 110 of the vessel. A shunt 102 has been inserted into the central lumen 110 of the blood vessel or body lumen along with the two non-removable open-strut type obturators 20. The clamp assists in stabilizing the vessel and providing ease of insertion of the shunt. The clamp may be placed upstream of the wound to provide hemostasis but not surround the wound as does the clamp shown in FIGS. 8A and 8B. Alternatively, the two clamps may be applied to the wound 100 prior to shunt placement. Here, one clamp is placed upstream of the wound and one clamp is placed downstream of the wound. This ensures full hemostasis during the shunt application. Following shunt placement and application of any clips (not shown), if desired to secure the vessel to the shunt, the vessel and shunt are de-aired and the clamps are removed.

If the vessel 40 is clamped off, the obturator 20, preferably, comprises one or more holes connecting the distal end to the proximal end of the obturator. These holes or openings are important to vent fluid or gas pressure trapped within the clamped vessel or body lumen. The holes may be connected to a fluid pressure source, for the purposes of pressurizing the vessel or body lumen prior or during insertion of the shunt 102 or 10 to assist with dilation of the vessel and insertion of the shunt. The fluid pressure source is, preferably, located at the proximal end of the two-piece shunt 10 or at the center of a one-piece shunt 102.

Figure 9A:
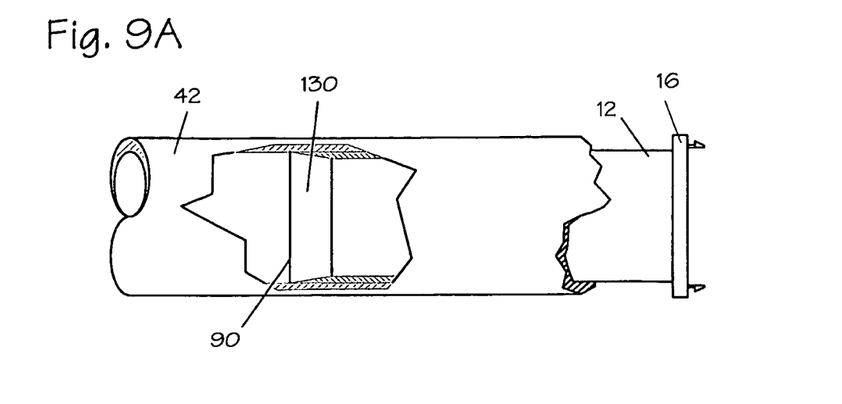
FIG. 9A illustrates a side view of one end of a severed body vessel or lumen with an outwardly flared shunt internal surface.

FIG. 9A illustrates another type of left shunt tube 12 or shunt end further comprising a distal edge 90, an internal outwardly flared distal region 130, and a flange 16, inserted into a severed end 42 of a damaged body vessel or lumen. The distal edge of the shunt left tube has a tapered or flared wall cross-section or internal outwardly flared distal region. The distal edge comes to a knife-edge or sharp edge in cross-section so that no ridges, ledges, bumps, or other features that could increase the risk of thrombosis or thrombo-embolism are present at this interface with the vessel end. The shunt left tube is rigid or may be elastomeric or deformable. The flared wall cross-section or internal outwardly flared distal region is, preferably rigid at its proximal end and becomes increasingly flexible or pliable at its distal end. The flared wall cross-section or internal outwardly flared distal region may also be entirely rigid. The flange provides attachment mechanisms to connect the shunt left tube to another shunt end. The description given herein describes the left shunt tube, but is illustrative of a right shunt tube, or any shunt end.

Figure 9B:
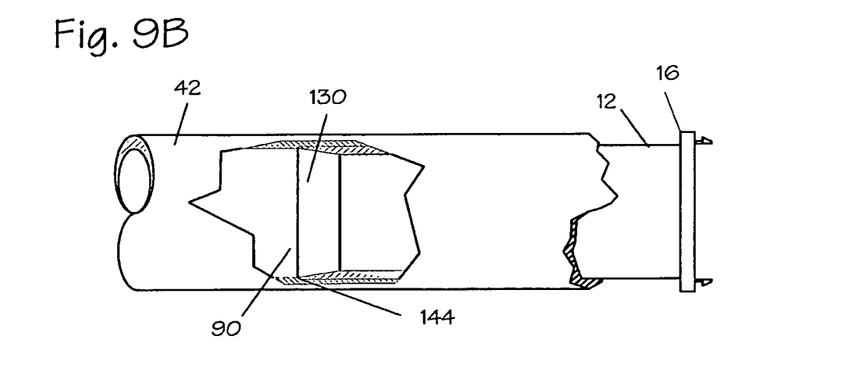
FIG. 9B illustrates a side view of one end of a severed body vessel or lumen with an outwardly flared shunt internal surface.

FIG. 9B illustrates another configuration of the left shunt tube further comprising a distal edge 90, an interior tapered or flared region or internal outwardly flared distal region 130, and a rounded or blunted exterior distal feature 144, and a flange 16, inserted into a damaged body vessel or lumen end 42. Here, the distal edge 90 of the shunt left tube 12 comprises a cross-sectional shape that is tapered at the internal outwardly flared distal region and meets with the vessel in a sharp edge without bumps or ridges, while the exterior aspect of the internal outwardly flared distal region is gently rounded to distribute stress on the body vessel or lumen. Such force distribution is beneficial to minimize tissue hyperplasia such as might form at a sharp distal edge tissue interface.

The shunt left tube 12 has an outer diameter that is slightly larger than the internal diameter of the body vessel or lumen 42. The body vessel or lumen is preferably measured, with respect to internal diameter, before placement of the shunt left tube thus permitting exact sizing of the shunt left tube prior to placement. With the outer diameter of the shunt left tube sized slightly larger than the vessel inner diameter, the shunt left tube makes an optimal seal with the elastomeric vessel and the knife-edge configuration of the distal shunt left tube 90 minimizes the risk of thrombosis and embolism. However, stresses on the vessel wall are increased because of this oversizing and the rounded exterior aspect 144 of the distal shunt left tube reduces or minimizes these stresses.

Figure 9C:
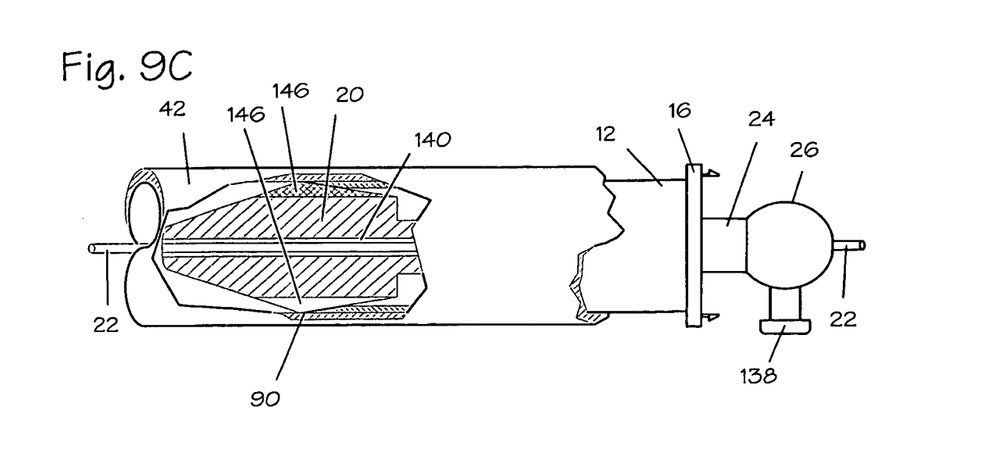
FIG. 9C illustrates a side view of one end of a severed body vessel or lumen with a shunt end and obturator inserted therein.

FIG. 9C illustrates the shunt left tube 12, depicted in FIG. 9A, further comprising an obturator 20, an obturator shaft 24, an obturator handle 26, a guidewire lumen 140, a guidewire 22, a flange 16, a collapsible region on the obturator 146 and an obturator release lever 138. The shunt left tube is inserted into a severed vessel end.

The shunt left tube 12 has a distal edge 90 that is formed with an internal flare or taper 130 that creates an undercut. The obturator 20 is configured to shield the distal edge 90 of the shunt left tube during insertion into the body vessel or lumen end 42. Withdrawal of the obturator back out of the proximal end of the shunt is difficult or impossible because of the undercut. The collapsing region 146 of the obturator permits the obturator to diametrically be reduced to a smaller size so as to be removed from the shunt left tube. The collapsing region may be fabricated from soft, elastomeric materials such as, but not limited to, C-Flex, silicone elastomer, or polyurethane that will compress upon withdrawal of the obturator. The collapsing region may also be configured like a split collet and activation of the obturator release lever 138 moves an interconnecting linkage (not shown), disposed within the obturator shaft 24 and connecting with the collapsing region 146. The interconnecting linkage (not shown) forces a diameter reduction in the collapsing region and permits subsequent removal of the obturator.

In FIG. 9C, the obturator 20 comprises the collapsing region 146. The collapsing region comprises a split collet structure fabricated from shape-memory components. The split collet structure in the obturator may or may not be further encased in an elastomeric or malleably deformable outer sheath to hide the collet. The split collet is configured so that when exposed to temperatures above its austenite finish temperature, the collet collapses to a diameter smaller than the inner diameter of the shunt left tube 12, thus permitting removal out of the proximal end. While in the martensitic phase, however, the collet of the obturator collapsing region is configured to be large enough in diameter to completely or partially cover the distal edge 90 of the shunt left tube.

As the temperature is increased, the shape memory materials will start in a martensitic configuration below austenite start temperature (As). As the temperature is further increased, the material becomes increasingly austenitic and less martensitic. When the temperature exceeds the austenite finish temperature (Af), the material will be fully austenitic. Due to hysteresis, the temperatures at which the martensite and austenite conditions occur while the temperature is decreasing will be different than those when the temperature is being increased. The austenite finish temperature is generally set to between 28 and 32 degrees Centigrade. When the shunt left tube is initially inserted into the vessel end, the temperature of the shunt left tube and obturator will be closer to room temperature (around 20 to 22 degrees centigrade). After the shunt left tube and obturator have been placed within the body for a while, the temperatures will increase to stabilize at or near 37 degrees centigrade. Once the temperature exceeds the austenite finish temperature, the obturator will have collapsed, thus permitting removal. A thermal mass or thermal capacitance (not shown) may also be added to control the amount of time that passes between insertion of the shunt left tube and the time when the obturator can be removed from the shunt left tube.

Figure 10A:
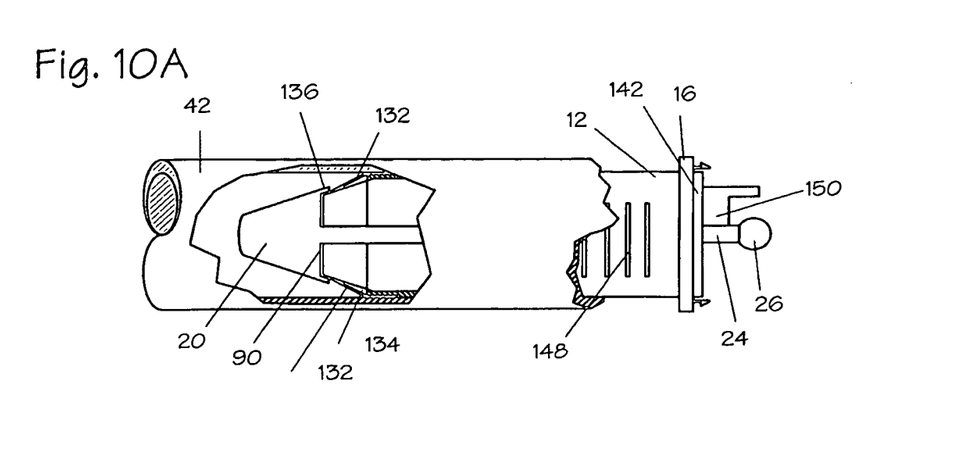
FIG. 10A illustrates a side view of one end of a severed body vessel or lumen with a shunt end and obturator inserted therein, the shunt end and obturator inserted therein.

FIG. 10A illustrates another configuration of the left shunt tube inserted into a severed vessel end 42. Here, the shunt left tube 12 further comprises a flange 16, an obturator 20, an obturator rod 24, an obturator handle 26, an obturator plate 142, an obturator lock 150, a collapsible shunt distal end 134, a plurality of shape-control elements 132, a plurality of calibration marks 148, and a shunt distal edge 90. The obturator 20 further comprises an internal lip 136.

Here, the shape-memory elements 132 are longitudinally oriented spring fingers or rods that are compressed by the internal lip 136 of the obturator 20. The distal ends of the shape-memory elements 132 are, preferably embedded within the collapsible shunt distal end 134 while the proximal ends of the shape-memory elements are preferably, but not necessarily, embedded in the more rigid shunt tube 12 wall material proximal to the collapsible shunt distal end. Alternatively, the shape-memory elements are at least partially circumferentially arrayed bands of material such as nitinol. Temperature changes caused by insertion of the shunt tube into the body vessel or lumen end 42 cause the shape-memory elements to enlarge or unwind circumferentially to cause the diameter increase of the collapsible shunt distal end. Simple removal of the obturator is another way to permit a shape memory, superelastic nitinol, or simple spring action device to cause outward expansion.

Once the shunt left tube has been inserted within the damaged or severed body lumen or vessel end with the aid of the obturator, the obturator lock is released, allowing the obturator rod to slide axially relative to the obturator plate. The obturator plate is pressed into or mated with the flange further secured by an optional plate lock, not shown. After release of the obturator lock the obturator handle is advanced distally, forcing the obturator rod and the obturator to move distally also. The obturator internal lip slides off the distal edge of the shunt left tube allowing the shape control elements to force the collapsible shunt distal end to open up. The shape-memory elements are fabricated from materials such as, but not limited to, Elgiloy, nitinol, titanium, stainless steel, and the like.

The obturator, the obturator shaft, the obturator knob or handle, the obturator lock and the obturator plate are fabricated from polymeric materials such as, but not limited to, ABS, PVC, polypropylene, polyethylene, polyimide, polyacetal, and the like.

The calibration marks are etched, inked, raised, embossed, molded, or colored to stand out from the background of the external surface of the shunt left tube. The calibration marks are important for determining how far the shunt has been inserted into the vessel end. The marks preferably show the acceptable range of insertion as evidenced by the position of the end of the vessel end relative to the calibration marks.

Figure 10B:
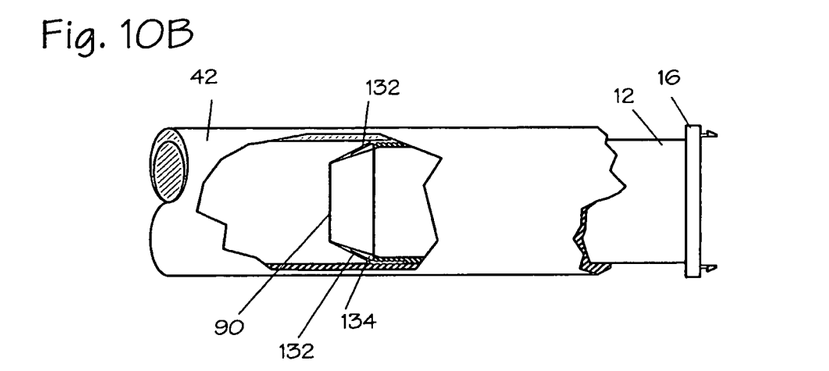
FIG. 10B illustrates a side view of one end of a severed body vessel or lumen with a shunt end inserted therein, the shunt end further comprising a collapsible distal end inwardly formed into a cone configuration.

FIG. 10B illustrates another configuration of the shunt left tube 12 inserted into the severed vessel end 42. Here, the shunt left tube further comprises a flange 16, a collapsible shunt distal end 134, a plurality of shape-control elements 132 and a shunt distal edge 90. In this embodiment, the shape-control elements are, preferably shape-memory elements such as nitinol fingers that expand upon exposure to body temperature. The shape-memory elements are preferably, but not necessarily, surrounded or encased by elastomeric or malleably deformable materials. The austenite finish temperature of the shape-memory elements is preferably between 28 and 32 degrees centigrade. The nitinol may include either equi-atomic or nickel-rich chemistries.

Figure 10C:
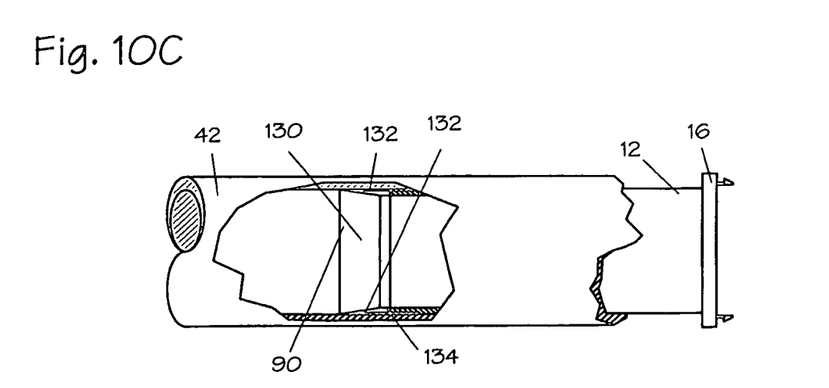
FIG. 10C illustrates a side view of one end of a severed body vessel or lumen with a shunt end inserted therein, the shunt end comprising a collapsible end restored.

FIG. 10C illustrates the shunt left tube 12 of either FIG. 10A or 10B wherein the collapsible shunt distal end 134 has expanded to align itself with the wall of the vessel end 42 into which the shunt left tube has been inserted. The shunt left tube further comprises a flange 16, a plurality of shape-memory elements 132, a collapsible shunt distal end 134, a sharp edge shunt distal edge 90, and an internally flared aspect of the shunt distal end 130. Here, the shunt distal edge is flush with the internal diameter of the vessel wall so no ridges or edges are presented. The shunt left tube is sized with an external diameter equal to or slightly greater than that of the internal diameter of the vessel end.

The application of fibrin glue or other hemostatic agents or bonding agents to seal the shunts 10 or 102 to the body vessel or lumen 40 is optional. In addition, anti-thrombogenic coatings, which typically bond heparin to the interior surface of the shunt, are optional. Such coatings are typically attached with covalent or ionic bonds. The exterior surfaces of the shunts are optionally coated with iodine or other antibacterial agent. The shunts are always supplied sterile in single or double aseptic packaging. Preferred sterilization methods include 25 to 40 kGray of Cobalt 60 radiation, although E-beam, autoclave, and ethylene oxide sterilization will also work. The shunts are preferably supplied in kits with a plurality of sizes and types of shunts provided in the kit. In addition, the kits optionally but preferably include a plurality of clamps 120, suture, sponges, bandages, forceps, scalpels, pharmaceutical agents, and the like.

The shunt may comprise a bifurcated or "Y" configuration capable of re-connecting a severed or damaged body lumen or vessel bifurcation or junction. An even greater number of severed or damaged vessels may be attached together using a manifold or multiple junction-style shunt.

Application of the temporary vessel shunt provides improved speed of blood vessel and other body duct trauma repair and minimizes the amount of hemorrhage and infection. The shunt provides for hemostasis and patency in blood vessels such as arteries and veins. The shunt prevents the further loss of fluids from a body duct and provides patency for that body duct or lumen. The shunt also provides for contamination control in the case where the body lumen or vessel is a bowel or intestine.

Once the shunt has been placed, a temporary wound closure may be placed over the skin surrounding the wound where the shunt is placed. This wound closure is fabricated from a material that has skin and wound contact surfaces that are impermeable to water, blood and tissue penetration. Preferably, these wound closure devices are fabricated from sheets of materials such as, but not limited to, polyurethane, polypropylene, polyethylene, silicone elastomer, and the like. The skin contact surface is a biocompatible adhesive and is further impregnated with anti-microbial agents such as, but not limited to, iodine, betadine and the like. The bandage or wound closure device is large enough to completely surround the wound and seal in the wound so that blood cannot escape. The bandage, optionally, has additional straps that fully surround the body or appendage and seal with Velcro, buckles, clamps or the like. The bandage or wound closure device seals the wound against the full systolic blood pressure and, thus tamponade any bleeding that occurs from damaged vessels other than the one repaired with the shunt.

The preferred wound closure is a large piece of Ioban®, a trademark and product of 3M Corporation, the non-adhesive side of which is adhered to a piece of woven gauze or mesh to provide adequate structure to the weak membrane of the Ioban. The Ioban has adhesive and anti-microbial properties preferred for this application. A strap extending from opposing ends of the bandage and terminated with Velcro assists in maintaining pressure against the wound and proving full tamponade of the hemorrhage. The central part of the skin contact region may also be comprised of a malleable or conformable pad, preferably adhered to the wound closure device, which helps to exert hemostatic force on the wound. The liquid-impermeable region of the wound closure device is preferably surrounded by a dam or seal to prevent the loss of blood from the environs of the wound. The conformable pad evenly distributes the forces throughout the wound so that no areas receive either too high a pressure, or too Iowa pressure, such as would permit further bleeding. The conformable central pad may be a block of foam covered by the aforementioned impermeable layer, or it may be an impermeable membrane filled with liquid such as saline, gel, or even a particulate material such as, but not limited to, sand, flour, sugar or the like. Typical wound closure devices appropriate for this procedure are described in U.S. provisional patent application No. 60/354,429, entitled "Method and Apparatus for Improved Hemostasis and Damage Control Operations", and U.S. provisional application No. 60/424,038, entitled "Method and Apparatus for Emergency Vessel Anastomoses", the full specifications of which are included herein by reference.

The implantable nature of these shunts facilitates damage control procedures wherein the patient can be allowed to stabilize prior to definitive repair of the injuries. Such damage control procedures have been shown to improve patient outcomes and save lives. These shunts are designed for ease of insertion and clamping under difficult circumstances.

The present invention may be embodied in other specific forms without departing from its spirit or essential characteristics. For example, the shunts may be implantable permanently, implantable for the long-term, or removable after only a short implant period. The shunts may be bioresorbable and ultimately disappear within the body. The shunts may be used on body ducts and lumens other than blood vessels. Clamping mechanisms and obturators may vary while maintaining the beneficial novels features. Methods of inserting the shunts may comprise the use of ultrasonic, X-ray, fluoroscopic, MRI, or infrared devices to guide said shunt insertion. The guiding devices may be separate or integrally mounted to the shunt.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:
1. An anastomosis device adapted for achieving patency and eliminating fluid loss in a severed vessel comprising:
   a first shunt comprised of an elongate tube with second and first ends and inner and outer surfaces wherein the second end of the shunt is configured to mate and seal with the second end of a second shunt;
   the second shunt comprised of an elongate tube with second and first ends and inner and outer surfaces wherein the second end of the shunt is configured to mate and seal with the second end of the first shunt;

a first obturator protruding from the first end of first shunt;

a second obturator protruding from the first end of second shunt;

a first clamp that secures the vessel around the outer surface of the first shunt: and a second clamp that secures the vessel around the outer surface of the second shunt;

wherein the first shunt is adapted for insertion into a first portion of the severed vessel and the second shunt is inserted into a second portion of the severed vessel and wherein the second ends of the shunts are engaged to each other to form a fluid pathway therethrough.

2. The device of claim 1 wherein the shunts are fabricated from bioresorbable material.

3. The device of claim 1 wherein the ends of the obturators are wire structures that angle inwardly to form a conical taper to facilitate insertion into a vessel, until exposed to body temperature at which time the wire transforms such that the obturator wires are oriented substantially parallel to the long axis of the shunt.

4. The device of claim 1 wherein at least a portion of each obturator comprises a collapsible region.

5. The device of claim 1 further containing a lumen positioned axially within the obturator for the enclosure of the guidewire.

6. The device of claim 1 wherein the clamps are spring-loaded.

7. The device of claim 1 wherein the clamps are elastomeric rolled tubes attached at to the second ends of the shunts.

8. The device of claim 1 wherein the obturator is tapered at its first end for insertion into the vessel.

9. The device of claim 1 further comprising a side port on the outer surface of the shunt for injection or withdrawal of fluids or air.

10. The device of claim 1 wherein the obturator has apertures at the second and first ends for ingress and egress of fluid within the obturator.

11. A temporary anastomosis device for achieving patency and eliminating fluid loss in a damaged vessel of the body, said device comprising:

a shunt comprising an axially elongate, flexible tube with second and first ends, an inner lumen, and inner and outer surfaces;

at least one obturator located at the first end of the shunt said obturator having a wire form tip adapted for insertion into the vessel, wherein the wire form tip is configured to permit fluid flow through the open regions of the wire form tip;

a loop disposed intermediate the first and second ends of the flexible tube, wherein the loop permits the distance between the first and second ends of the axially elongate flexible tube to vary;

at least one clamp adapted to secure the vessel around the outer surface of the shunt;

wherein the clamp is sized and dimensioned to surround the vessel around at least one end of the shunt, and said clamp is operable to secure the vessel to the shunt to create a substantially fluid-tight seal.

12. The device of claim 11 wherein the wire form tip of the obturator can comprise shape-memory materials that expand or reconfigure their shape in response to immersion in fluid at body temperature.

13. The device of claim 12 wherein the wire form tip of the obturator expands to minimize impingement of the wires on the flow lumen of the shunt or vessel.

14. The device of claim 11 further comprising a port for removing air from the shunt following connection to the damaged vessel of the body.

15. The device of claim 11 further comprising anti-thrombogenic coatings on the interior surfaces and the obturator.

16. A method of achieving patency and eliminating fluid loss in an opened body vessel or lumen tissue comprising the steps of:

providing a shunt device comprising an axially elongate tube dimensioned and configured to be inserted into the vessel, said tube having second and first ends, inner and outer surfaces, an inner lumen, and an obturator on at least one end of the tube, wherein the obturator comprises open wires that taper inwardly moving away from the shunt;

preparing the damaged body vessel or lumen tissue site by drawing ends of the damaged vessel or lumen together;

inserting the first end of the tube into the vessel with the tapered obturator facilitating entry of the first end of the tube into the vessel;

securing a clamp about the vessel at the first end of the tube to seal the first end to the vessel;

inserting the second end of the tube into the vessel with the tapered obturator facilitating entry of the second end of the tube into the vessel; and securing a clamp about the vessel at the second end of the tube to seal the second end to the vessel.

17. The method of claim 16 further comprising the step of forming a loop in the axially elongate tube and positioning the first and second ends to best span the distance between the two ends of the severed body vessel or lumen tissue.

18. The method of claim 16 further comprising the step of withdrawing air from inside the axially elongate tube through a port pre-attached to the axially elongate tube.

19. The method of claim 16 further comprising the step of expanding the inwardly tapered ends of the obturator such that the inwardly tapered ends are parallel to, or angled slightly outward relative to, the wall of the vessel.

20. The method of claim 16 further comprising the step of coating the interior of the axially elongate tube and the obturator with anti-thrombogenic material.

* * * * *